United States Patent [19]

Veber et al.

[11] 4,066,749

[45] Jan. 3, 1978

[54] TETRAPEPTIDE ANALOG OF TRH

[75] Inventors: Daniel F. Veber, Ambler; Ruth F. Nutt, Green Lane; Ralph F. Hirschmann, Blue Bell, all of Pa.

[73] Assignee: Merck & Co., Inc., Rahway, N.J.

[21] Appl. No.: 761,760

[22] Filed: Jan. 24, 1977

[51] Int. Cl.$^2$ .................... A61K 37/00; C07C 103/52
[52] U.S. Cl. ........................ 424/177; 260/112.5 TR
[58] Field of Search ............... 260/112.5 TR; 424/177

[56] References Cited

U.S. PATENT DOCUMENTS 3,959,248  5/1976  Veber et al. ...................... 424/177

FOREIGN PATENT DOCUMENTS 832,783  2/1976  Belgium .............................. 424/177

OTHER PUBLICATIONS

Willson, et al.; Biopolymers, 15, 2317 1976.

*Primary Examiner*—Delbert R. Phillips
*Attorney, Agent, or Firm*—Harry E. Westlake, Jr.; William H. Nicholson

[57] ABSTRACT

A novel tetrapeptide L-2-ketopiperidine-6-carbonyl-L-histidyl-L-thiazolidine-4-carbonyl-$\beta$-alanin-amide, (L-Kpc-L-His-L-Tca-$\beta$-ala-NH$_2$), is a stimulant of the central nervous system. It is preparable by standard peptide synthetic procedures.

5 Claims, No Drawings

TETRAPEPTIDE ANALOG OF TRH

BACKGROUND OF THE INVENTION

This invention is concerned with a tetrapeptide, L-2-ketopiperidine-6-carbonyl-L-histidyl-L-thiazolidine-4-carbonyl-β-alaninamide (L-Kpc-L-His-L-Tca-β-ala-NH₂) or a pharmaceutically acceptable salt thereof which is useful as a central nervous system stimulant with a rapid onset of action and a minimum of adverse side effects.

Thyrotropin releasing hormone (TRH) is a naturally-occurring, well-known tripeptide, L-pyroglutamyl-L-histidyl-L-prolinamide. Besides its hormone releasing activity it is also known to have antidepressant activity.

Recently several publications have reported the preparation of derivatives and analogs of TRH with a view to augmenting the antidepressant activity of TRH. Veber et al., in U.S. Pat. No. 3,959,248, describes a group of compounds analagous to TRH which manifests an increased antidepressant activity and/or decreased hormone releasing activity. Belgian Pat. No. 832,783 describes a TRH derivative in which the amide nitrogen, proline amide, is substituted with a 2-carbamylethyl group resulting in the tetrapeptide amide, L-pyroglutamyl-L-histidyl-L-prolyl-β- alaninamide which also manifests an increased antidepressant activity relative to the hormone releasing activity.

The novel compound of this invention, L-Kpc-L-His-L-Tca-β-ala-NH₂, displays greater activity as a central nervous system stimulant than does TRH.

DETAILED DESCRIPTION OF THE INVENTION

The novel compound of the present invention is a tetrapeptide amide of formula:
L-Kpc-L-His-L-Tca-β-Ala-NH₂
or a pharmaceutically acceptable salt thereof, wherein L-Kpc is L-2-ketopiperidine-5-carbonyl, 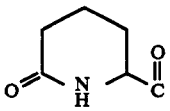

L-His is L-histidyl, 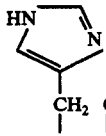

L-Tca is L-thiazolidine-4-carbonyl, 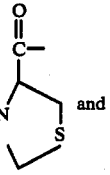 and

β-Ala is β-alanyl,  $H_2NCH_2CH_2-C-$ .

The pharmaceutically acceptable salts contemplated to be within the scope of the present invention are those prepared from inorganic or organic acids known in the art to provide pharmaceutically acceptable salts, such as hydrochloric, sulfuric, hydrobromic, phosphoric, cyclohexylcarboxylic, tartaric, fumaric, citric, malic, maleic, ascorbic, acetic, lactic, aleic pamoic, palmitic, isethionic acid, pyroglutamic acid or the like.

The novel process of the present invention comprises formation of an amide or peptide bond between the carboxyl group of one moiety of the tetrapeptide and the amino group of another moiety as illustrated by the following equations:

1. L-Kpc-OH + L-His-L-Tca-β-Ala-NH₂→

2. L-Kpc-L-His-OH + L-Tca-β-Ala-NH₂→

3. L-Kpc-L-His-L-Tca-OH + β-Ala-NH₂→

4. L-Kpc-L-His-L-Tca-β-Ala-OH + NH₃→

It is understood, that, although not shown above, the amino acid or peptide starting materials may have amino blocking groups to protect those amino groups not intended to take part in peptide band formation. For example, the histidine group in Equations (2), (3) and (4) has an inidazole nitrogen which may be protected from participation in peptide bond formation. Many suitable protective groups are recognized in the art for this purpose, a common one being 2,4-dinitrophenyl (DNP) tosyl or benzyl. Similarly, the ring nitrogen of L-Kpc (L-2-ketopiperidine-6-carbonyl) may be protected by an art recognized blocking group but in this instance is usually not required. Common amino blocking groups employed for this purpose in peptide chemistry are the benzyloxycarbonyl, or t-butyloxycarbonyl (Boc) group.

Peptide bond formation may be accomplished in any one of several methods falling into two general classes: (1) direct coupling of a carboxyl and an amino group; or (2) coupling of a carboxyl derivative with an amino group. The direct coupling generally requires a coupling agent to promote the condensation such as cyclohexylcarbodiimide, either alone or in combination with 1-hydroxybenzotriazole or N-hydroxysuccinimide; triphenylphosphite and imidazole; triphenylphosphine and dipyridyl-2, 2'-disulfide; or Woodward's reagent. In the second case useful carboxyl derivatives are azides, halides, mixed anhydrides, or active esters such as p-nitrophenyl, N-hydroxysuccinimidyl, perfluorophenyl, cyanomethyl, p-nitrophenylthio, and the like.

The coupling is normally conducted in an anhydrous inert organic solvent such as dimethyl formamide or chlorinated hydrocarbons such as chloroform, methylene chloride, 1,2-dichloroethane, or the like, at temperatures from about 0° C. to about 25° C.

The reaction represented by Equation (3) supra is particularly suitable for preparing the novel compound of the present invention, and generally nitrogen protecting groups are not necessary. The reaction comprises mixing the tripeptide, L-Kpc-L-His-L-Tca-OH with from 1-1.5 equivalents of β-Ala-NH₂, at least 1 equivalent of 1-hydroxybenzotriazole and an equivalent of dicyclohexylcarbodiimide in dimethyl formamide at room temperature and allowing the reaction to proceed for about 10 to about 20 hours.

The novel compound of the present invention is a central nervous system stimulant and may be used for treating mammals suffering from central nervous system depression. It may be administered by any convenient method, e.g. orally, parenterally, intravenously, sublingually, by insulfation, by suppository, or the like.

Dosage levels adequate to produce the desired effect are used. Generally, the dosage range will be from 0.05 to 100 mg. per dose, administered alone, or in combination with accepted pharmaceutical carriers.

EXAMPLE 1

L-2-ketopiperidine-6-carbonyl-L-histidyl-L-thiazolidine-4-carbonyl-β-alaninamide
(L-Kpc-L-His-L-Tca-β-ala-NH$_2$)

Step A: Preparation of β-alaninamide.HCl (β-ala-NH$_2$.HCl)

Boc-β-ala-OH (10 g.) was dissolved in diluted ammonium hydroxide and freeze dried to give 10.79 g. (0.053 mole) of ammonium Boc-β-alaninate (Boc-β-ala-ONH$_4$).

A mixture of this material, 10.8 g. of 1-hydroxybenzotriazole (HBT), 5.67 g. of ammonium chloride, and 100 ml. of methylene chloride was cooled to 0° C. and treated with 10.9 g. of dicyclohexylcarbodiimide (DCCI) and 9.17 ml. of di(isopropyl)ethylamine. After 45 minutes, 11 ml. of di(isopropyl)ethylamine was added (pH 7.6–8). After a total of 1.5 hours, the mixture was filtered. The solid was extracted with dimethyl formamide and the extract was concentrated in vacuo to 7.82 g. of residue. The residue was crystallized from hot isopropanol solution by the addition of about 400 ml. of petroleum ether to give 3.82 g. of crude product which on recrystallization from isopropanel-n-hexane gave 3.43 g. of Boc-β-ala-NH$_2$, m.p. 161.5– 163

This material, 600 mg., was suspended in 6 ml. of ethyl acetate, cooled to −25° C., and treated with hydrogen chloride for 5 min. Excess hydrogen chloride was purged with nitrogen at 0° C. for 5 min. The product (β-ala- NH$_2$.HCl) was precipitated by dilution with ether, collected, washed with ether and used directly in the next step without characterization.

Step B: Preparation of methyl L-thiazolidine-4-carboxylate hydrochloride (L-Tca-OCH$_3$.HCl)

A suspension of 10 g. of thiazolidine-4-carboxylic acid (L-Tca-OH) in 100 ml. of methanol was cooled in an ice-bath and treated dropwise with 20 ml. of thionyl chloride with stirring. Stirring was continued overnight at room temperature. The mixture was concentrated to dryness in vacuo, and the residue was stirred with 100 ml. benzene. The crystalline product was collected on a filter to give 13.41 g. (97%) of methyl L-thiazolidine-4-carboxylate hydrochloride, $[\alpha]_D$ −77.14° (c, 1 in methanol). m.p. 164°–166.5° C.

Step C: Preparation of L-Boc(DNP)his-L-Tca-OCH$_3$

A mixture of 6 g of L-Tca-OCh$_3$.HCl, 13.7 g. of L-Boc(DNP)His-OH, and 7.5 g. of 1-hydroxybenzotriazole hydrate was suspended in 100 ml. of methylene chloride, and 7.71 g of dicyclohexylcarbodiimide was added with stirring and di(isopropyl)ethylamine was added in small increments as needed to control the pH at about 7, 19.3 ml. being added over a 1 hour period. An additional 100 ml. of methylene chloride was added during the reaction. After ad additional 1.5 hours of stirring, the mixture was filtered and the filtrate was evaporated in vacuo. The residual oil was dissolved in 400 ml. of ethyl acetate and extracted with sodium bicarbonate solution (3 × 150 ml.), citric acid solution (1 × 150 ml.), water (1 × 100 ml.) and sodium bicarbonate solution (1 × 50 ml.), dried over magnesium sulfate, filtered and concentrated to dryness in vacuo to give 8.78 g. of residue. The residue was dissolved in 75 ml. of isopropanol and diluted with 500 ml. of petroleum ether. The supernatant was decanted from 5.73 g. of a gummy solid. This material was chromatographed on 600 g. of silica gel by elution with chloroform:isopropanol (95:5 v/v) and collecting 70 ml. fractions/minute. Fractions 20–45 were collected and concentrated to dryness in vacuo to give 2.42 g. of residue. The residue was rechromatographed on 300 g. of silica gel by elution with chloroform (1 .l) 2% (v/v) isopropanol in chloroform (2 l), 3% (v/v) isopropanol in chloroform (3 l), and 5% (v/v) isopropanol in chloroform (1 l). The fractions containing the product were combined and concentrated to dryness to give 1.24 g. of L-Boc(DNP)-his-L-Tca-OCH$_3$.

Step D: Preparation of L-(DNP)His-L-Tca-OCH$_3$.2HCl

L-Boc(DNP)his-L-Tca-OCH$_3$ (1 g.) was suspended in 25 ml. of ethyl acetate, cooled to −25° C. and treated with gaseous hydrogen chloride for 5 minutes. Excess hydrogen chloride was purged with nitrogen at 0° for 5 min. The product was precipitated by dilution ether, collected, and washed with ether to give 980 mg. of L-(DNP)His-L-Tca-OCH$_3$.2HCl.

Step E: Preparation of L-Kpc-L-(DNP)His-L-tca-OCH$_3$

A mixture of 1 g. of L-(DPN)His-L-Tca-OMe.2HCl, 358 mg. of L-Kpc-OH, and 438 mg. of 1-hydroxybenzotriazole. H$_2$O was suspended in 20 ml. of methylene chloride. To the suspension was quickly added 0.657 ml. of di(isopropyl)-ethylamine and 1.0 ml. of a solution of dicyclohexylcarbodiimide (1.275 g. in 2.7 ml. of methylene chloride solution). During the next 10 minutes small increments (0.05 to 0.2 ml.) of di(isopropyl)ethylamine were added (0.75 ml. total). After a reaction time of 0.5 hour, the mixture was filtered, washed with methylene chloride, and the filtrate was concentrated in vacuo. The residue was triturated twice with petroleum ether, the solvent being decanted, dissolved in 2 ml. of methylene chloride, precipitated with petroleum ether and concentrated to dryness in vacuo (3.21 g.). The residue was dissolved in 100 ml. of ethyl acetate and extracted with 3 × 30 ml. of water. The combined aqueous extracts were extracted with 3 × 25 ml. of methylene chloride. The ethyl acetate and methylene chloride solutions separately were dried, concentrated to dryness to give a total of 1.51 g. of material.

This material was chromatographed on 150 g. of silica gel by elution with chloroform:methanol:water (90:10:1 v/v/v) collecting 30 ml. fractions/1.5 min. Fractions 12–17 were combined and concentrated to dryness to give 360 mg. of product.

The other fractions containing product were combined and rechromatographed on 70 g. of silica gel by elution with chloroform:methanol:water (95:5:0.5 v/v/v). Combination and concentration of the appropriate fractions provided additional material which combined with the previous material gave 950 mg. of L-Kpc-L-(DNP)His-L-tca-OCH$_3$.

Step F: Preparation of L-Kpc-L-His-L-Tca-OMe

The product from Step E (950 mg.) was dissolved in 27 ml. of dimethyl formamide and treated with 3 ml. of 2-mercaptoethanol at room temperature. After 30 min. the solution was concentrated to dryness. Five times the residue was dissolved in ethyl acetate and oiled out by addition of petroleum ether. The residue was dissolved in ethyl acetate and extracted three times with water. The water extract was concentrated to a volume of 50 ml.

Step G. Preparation of L-Kpc-L-His-L-Tca-OH

The above aqueous solution of methyl ester was treated with 5 drops of 11 N sodium hydroxide solution. After 45 mins. 7 drops of 50% acetic acid were added (pH 7) and the mixture was concentrated to dryness (920 mg.).

The residue was chromatographed on 125 g. of silica gel by elution with chloroform:methanol:water (60:30:5 v/v/v) (60:40:10 v/v/v after fraction 20) collecting 30 ml. fractions/1.5 mins. Fractions 25–42 were combined and concentrated to dryness to give 470 mg. of L-Kpc-L-His-L-Tca-OH.

Step H. Preparation of L-Kpc-L-His-L-Tca-β-ala-NH₂

A mixture of 201.18 mg. of L-Kpc-L-His-L-Tca-OH, 95.49 mg. of β-ala-NH₂.HCl, 171.00 mg. of 1-hydroxybenzotriazole hydrate, 2 ml. of dimethyl formamide, and 0.13 ml. of di(isopropyl)ethylamine was treated with 118.65 mg. of dicyclohexylcarbodiimide and kept overnight at room temperature. The mixture was diluted with 20 ml. of water, filtered, and the filter was washed with 20 ml. water. The filtrate was passed through a column of Dowex 1×2 acetate and eluted with water. The desired fractions of eluate were combined and concentrated in vacuo to 500 mg. of oil. Trituration with ethyl acetate gave approximately 320 mg. of crude product. Combination of this material with that of previous runs gave 440 mg. which was chromatographed on 40 g. of silica gel by elution with chloroform:methanol:Conc.NH₄OH (80:20:2 v/v/v), collecting 25 ml. fractions/1.5 min. Fractions 15–27 were combined and concentrated to dryness to give 210 mg. of L-Kpc-L-His-L-Tca-β-ala-NH₂.

What is claimed is:

1. A process for the preparation of the compound of formula:

L-Kpc-L-His-L-Tca-β-Ala-NH₂ or a pharmaceutically acceptable salt thereof, which comprises the formation of a peptide bond between:
1. L-Kpc-OH and L-His-L-Tca-β-Ala-NH₂;
2. L-Kpc-L-His-OH and L-Tca-β-Ala-NH₂;
3. L-Kpc-L-His-L-Tca-OH and β-ala-NH₂; or
4. L-Kcp-His-L-Tca-β-Ala-OH and NH₃.

2. The process of claim 1 which comprises the formation of a peptide bond between L-Kpc-L-His-L-Tca-OH and β-Ala-NH₂.

3. The compound of formula:

L-Kpc-L-His-L-Tca-β-Ala-NH₂ or a pharmaceutically acceptable salt thereof.

4. A method of treating central nervous system depression which comprises administration to a patient in need of such treatment an effective amount of a compound of formula:

L-Kpc-L-His-L-Tca-β-Ala-NH₂ or a pharmaceutically acceptable salt thereof.

5. A pharmaceutical composition comprising a pharmaceutical carrier and an effective amount of a compound of formula:

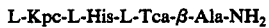
L-Kpc-L-His-L-Tca-β-Ala-NH₂ or a pharmaceutically acceptable salt thereof.

* * * * *